United States Patent [19]

Leiner et al.

[11] Patent Number: 4,755,684
[45] Date of Patent: Jul. 5, 1988

[54] METHOD FOR TUMOR DIAGNOSIS AND ARRANGEMENT FOR IMPLEMENTING THIS METHOD

[75] Inventors: Marc Leiner, Heinerscheid, Luxembourg; Rudolf J. Schaur, Graz, Austria

[73] Assignee: AVL AG, Schaffhausen, Switzerland

[21] Appl. No.: 905,558

[22] Filed: Sep. 10, 1986

[30] Foreign Application Priority Data

Sep. 16, 1985 [AT] Austria ................................. 2703/85

[51] Int. Cl.⁴ ............................................ G01N 21/64
[52] U.S. Cl. ............................... 250/461.1; 250/461.2
[58] Field of Search ................ 128/653, 634, 637; 250/461.1, 461.2, 459.1, 328, 458.1; 356/39, 317, 318

[56] References Cited

U.S. PATENT DOCUMENTS

| | | | |
|---|---|---|---|
| 3,327,117 | 6/1967 | Kamentsky | 128/653 |
| 3,973,129 | 8/1976 | Blumberg et al. | 250/461 B |
| 4,131,800 | 12/1978 | Bruck et al. | 250/461 B |
| 4,419,583 | 12/1983 | Noeller | 250/458.1 |
| 4,476,870 | 10/1984 | Peterson et al. | 128/634 |
| 4,560,286 | 12/1985 | Wickersheim | 374/131 |

*Primary Examiner*—Janice A. Howell
*Attorney, Agent, or Firm*—Watson, Cole, Grindle & Watson

[57] ABSTRACT

In contrast to relatively expensive known methods for tumor diagnosis by means of serum tests, the serum to be investigated (or its albumin or globulin subfraction) are excited by an excitation radiation at least of a wavelength between 250 and 300 nm, and its fluorescence intensity is measured at predetermined emission wavelengths. From deviations of these measuring values from those of a standard or standard serum a conclusion can be drawn with respect to the presence of neoplastic diseases.

14 Claims, 5 Drawing Sheets

METHOD FOR TUMOR DIAGNOSIS AND ARRANGEMENT FOR IMPLEMENTING THIS METHOD

BACKGROUND OF THE INVENTION

The invention relates to a method for tumor diagnosis by means of sera and an arrangement for implementing this method.

The considerable interest which exists nowadays for an early and reliable tumor diagnosis has led to the examination of many analytical methods for their possible usefulness for tumor diagnosis. The search for tumors in different tissues or organs is rather laborious, since in this case a great number of specimens have to be taken and the preparation of cell specimens from difficulty accessible organs is a major obstacle for early tumor diagnosis when a large population should be screened. Especially for screening purposes, direct investigations of serum should be favored in comparison to all other methods.

Special attention has been paid to the investigation of human serum, because its preparation belongs to routine procedures in clinical analysis. Therefore, serum can be obtained from many persons easily and rapidly. This is of particular importance for screening purposes.

DESCRIPTION OF THE PRIOR ART

The main role for the diagnosis of malignant tumors by way of serum tests is played by the so called tumor markers. Tumor markers are any parameters which can give indications of a neoplastic process. Among the known, relatively expensive procedures for tumor diagnosis, immunological methods are applied above all other methods.

SUMMARY OF THE INVENTION

It is an object of this invention to provide a method which makes possible in a simple way and with relatively high accuracy the differentiation between normal sera and tumor sera, and to present an arrangement for the execution of this method.

According to the invention this aim is achieved by exciting the serum to be investigated, or its albumin or globulin fraction, by radiation of at least one wavelength between 250 and 300 nm, by measuring the fluorescence intensity of the serum at predetermined emission wavelengths, by determining deviations of these measuring values from those of a standard or standard serum, and drawing conclusions about the presence of neoplastic diseases from these deviations. These steps provide a novel spectroscopic method for tumor diagnosis that takes advantage of the fact that the emission optical properties of normal serum are slightly but unequivocally different from those of a tumor serum and its protein subfractions. The fluorescence spectrum of normal serum displays an emission maximum at about 337 nm, which stems predominantly from protein-bound tryptophan (Trp).

In one elaboration of the invention, the fluorescence intensity of the sample to be investigated is measured at an emission wavelength of above 340 nm, normalized in intensity, e.g., to the peak maximum value, and compared with the fluorescence intensity of a standard or standard serum. A decrease of the normalized fluorescence intensity allows conclusions to be drawn with respect to the presence of neoplastic diseases, since the fluorescence spectra of human serum samples are changed in a very characteristic way with the appearance of neoplastic diseases. These changes occur, for instance, at the long wavelength side of the spectrum, where they are especially well developed.

In order to discern deviations of the normal spectral distribution of the fluorescence, it is not sufficient to determine solely the fluorescence intensity, since the absolute fluorescence intensity varies from serum to serum. In order to exclude such variations it is necessary to normalize the fluorescence intensity by relating it to the intensity at the emission maximum of the spectrum. For this purpose the fluorescence intensity $I_o$ of diluted (e.g., dilution with water 1:200–1:1000) human serum or its protein fractions is determined at the emission maximum, i.e., at about 337 nm. In a second measurement the fluorescence intensity $I_x$ is determined at the long-wavelength side of the emission spectrum, i.e., in the wavelength range between 350 and 400 nm, with an excitation wavelength between 250 and 300 nm, typically at 287 nm. The ratio of both intensities ($I_x/I_o$) has to have a certain minimum value in case of healthy donors. In case the value falls below this minimum value, this is indicative for a tumor. This minimum value is determined by calibration with a standard. This standard can be, e.g., an averaged value from several sera of healthy persons or a synthetic standard, as for instance N-acetyl-L-tryptophanamide.

With sera of patients with cancerous diseases, decreases in the ratio of intensities as far as to a value of 0.636 were found, whereas in the normal case a ratio of 0.714 was observed. In each instance, a careful calibration of instrument has be carried out before a series of measurements is started. By measuring at two emission wavelengths (two-wavelengths measurement), a maximum probability for detection of cancerous diseases of 60% can be achieved. It is remarkable that no false positive cases were indicated.

The execution of the method by way of the two-wave-lengths measurement is simpler and more rapid than the taking of the normalized emission spectrum followed by subtraction of a stored normalized emission spectrum of a standard serum. This is an essential advantage with regard to the application within screening investigations.

In a subsequent eleboration of the invention it is considered to measure the fluorescence intensity of the serum or serum protein to be investigated at an additional emission wavelength between 320 and 330 nm, to normalize the fluoroscrence intensity, and to compare it with the fluorescence intensity of a standard serum. An increase of the normalized fluorescence intensity is indicative for the presence of neoplastic diseases. By inclusion of the short-wavelength side of the spectrum and measurement of intensity deviation in this region the accuracy of the method can be further increased. With the aid of this so-called three-wavelengths measurement, i.e., by the additional measurement of the fluorescence intensity $I_y$ in the short-wavelength region of the spectrum, the probability of true positive values can be substantially augmented.

With sera from healthy donors, the ratio $I_x/I_o$ may reach a certain minimum value and simultaneously the ratio $I_y/I_o$ may reach a certain maximum value. The corresponding values from sera of patients with neoplastic diseases fall below respectively above these limiting values. Similar effects are found with certain serum subfractions, e.g., albumin or globulin.

In another elaboration of the invention it is considered to measure the fluorescence intensity of the serum to be investigated both in a solution of physiological pH value and in an acidic solution with a pH value below 4, to normalize the fluorescence intensities and to draw a conclusion from the difference or the ratio of the normalized measuring values with respect to the presence of neoplastic diseases. An additional difference in the fluorescence-optical properties of sera of healthy and tumor-bearing persons, respectively, was found by studying the pH-dependence of the corresponding fluorescence properties. The emission maximum of human serum from healthy donors lies between 336.5 and 337.5 nm with very small variations (measured on an AMINCO SPF 500 instrument). In comparison with this maximum, the emission maximum of tumor sera is slightly shifted to shorter wavelengths. This applies for pH values in the physiological range.

However, when measuring a normal serum in highly acidic solution, e.g., in 0.1 M hydrochloric acid, a blue-shift of the emission maximum occurs when compared with the maximum at physiological pH. In contrast, with a tumor serum this maximum is only weakly or not at all shifted by decreasing the pH value. Thus, in highly acidic solution the emission maximum of tumor sera is weakly shifted to somewhat longer wavelengths when compared with the maximum of normal sera.

Hence, in highly acidic solution the Trp emission maximum of sera from patients with malignant tumors is red-shifted when compared with those of healthy persons. All deviations observed in the physiological pH range merely change their sign in acidic solution. Therefore, all of the measuring methods described above can be applied in the acidic pH range. However, different ratios of fluorescence intensities are found. As is the case in the neutral pH range, when measuring in the acidic range the mean value of individual ratios has to be determined empirically by arithmetical averaging a certain number of ratios of sera from healthy persons on with the aid of a standard.

When the measurements are carried out in the neutral as well as in the acidic pH range, there is no need to measure a large number of control sera to determine the normal range of fluorescence intensity ratios. Rather, only the intensities $I_o$ and $I_x$ in the physiological range and the intensities $I_o'$ and $I_x'$ in the acidic range have to be measured. When measuring in the long-wavelength-region the difference of the ratios ($I_x'/I_o'$ minus $I_x/I_o$) yields a negative value for sera of healthy persons. A positive value would be indicative for a tumor. Considering this fact the measuring method is independent from the precise situation of the normal range of ratios thereby rendering the calibration with a standard serum unnecessary.

In another elaboration of the invention it is considered to measure the fluorescence intensity of the serum to be investigated at at least one emission wavelength both in the presence and in the absence of a dynamic fluorescence quencher and to diagnose a neoplastic disease from the difference or the ratio. The quenching of fluorescence usually obeys the Stern-Volmer relationship $$I_o/I = 1 + K_{sv} \times (L)$$

In this equation $I_o$ means the fluorescence intensity of Trp in absence of a quencher, $I$ the fluorescence intensity in presence of a quencher with concentration (L), and $K_{sv}$ the quenching constant.

It was found that the fluorescence of serum from healthy persons can be quenched to a significantly higher extent by addition of a suitable quencher than the fluorescence of serum from tumor bearing persons.

Since quenching of fluorescence shows a wavelength dependence when applied to sera (the ration $I_o/1$ is constant for all wavelengths in a first approximation only), the possibility exists to use (another) ratio for drawing a conclusion about the presence of neoplastic disease. In the most simple way this can be done by determining the ratio of two fluorescence intensities $I_x$ and $I_y$, and $I_x'$ and $I_y'$, respectively, at two different emission wavelengths, e.g., 350 and 380 nm or 350 and 320 nm, in the absence and in the presence of a quencher. Then, for instance, the difference of ratio $I_x/I_y - I_x'/I_y'$ can be used for diagnosis. It is advantageous that another source of error can be avoided by measuring at two analytical wavelengths, namely, the existance of a so called inner filter effect of the quencher, which might lead to the absorption of excitation light even at low concentration.

Preferentially, iodide ions are used as dynamic fluorescence quencher, but others such as acrylamide, molecular oxygen and several other molecules also capable of reducing the fluorescence of protein-bound Trp.

To exploit this effect one can proceed using the following measuring practice: The serum of tumor-bearing persons is measured in diluted solution both in presence and in absence of, e.g., 0.1 M/liter potassium iodide. Then, the fluorescence intensities measured at 337 nm are compared.

An advantageous elaboration of the invention is given by the measurement of the fluorescence intensity at two different excitation wavelengths, preferably at 287 nm and 295 nm, and at three different emission wavelengths, preferably at 325, 337 and 365 nm. The highest precision for the three-wavelengths-measurement can be achieved by using two different excitation wavelengths. In order to make possible the measurement at two different excitation wavelengths simultaneously, one measuring cuvette is needed for each excitation wavelength. In one case, $I_o$ and $I_x$ are measured in the long-wavelengths region and in the second case $I_o'$ and $I_y'$ in the short-wavelengths region. With normal sera the ratio, $I_o/I_x$ may reach a certain minimum value and simultaneously the ratio $I_y'/I_o'$ a certain maximum value. The corresponding values from sera of patients with neoplastic diseases fall below respectively above these limiting values.

According to the invention an arrangement for implementing the method described is realized by exposing at least one sample cell, which contains the serum to be investigated, to the excitation radiation emitted by a light source and having passed through an optical filter. The sample cell is surrounded by at least one measuring device, consisting of an optical filter and a light detector. The signals from the latter are amplified and ratioed in a calculator unit. Thereby a simple arrangement is provided, in which the wavelength necessary for excitation is realized either by a light source emitting in this range or by a filter.

Rather than performing the tests previously described, it can be advantageous to submit protein subfractions of human serum to spectral investigations. Thus, the albumin or globulin subfractions may be purified by one of the conventional ways such as electrophoresis or chromatography, dissolved in water in a typical concentration of 0.1–0.3 mg per milliliter, and submitted to fluorimetry by one of the methods described before.

Another embodiment of the invention comprises two sample cells which can be supplied by way of one filter, each with light emitted from the same light source and having different wavelengths, if necessary. This variant of the arrangement is required for all of the measuring methods that involve the excitation of one sample with light of different wavelengths, or the addition of a substance influencing the fluorescence of the sample.

In a special elaboration of the invention an optical light guide such as a fiber for the excitation radiation is placed between the light source and the sample cell(s), and the emitted fluorescence radiation of the sample is transmitted to each measuring device by means of further light guides. By combining the light guides into a bundle it is possible to design the latter as an invasive catheter and to perform in-vivo measurements in whole blood.

In a further elaboration of the invention it is considered to use one light guide only per sample cell, which conducts both the excitation radiation and the fluorescence radiation, and to use a dichroic mirror or a deflecting mirror in order to separate the fluorescence radiation from reflected or scattered exciting light and to transmit it to the measuring device. Typically a light guide with a diameter between 100 and 150 micrometer is used for each combination of wavelengths, consisting of an excitation wavelength and an emission wavelength to be measured. The induced fluorescence light is transmitted to the corresponding measuring device with the aid of a ray distributor. It is also possible to couple several wavelengths successively into one optical fiber only, e.g., with the aid of a rotating filter wheel.

Finally, it is advantageous with regard to the invention, to user sample cell formed of a protein-permeable membrane, preferably a cellulose membrane, which is attached to that end of the light conductor which is close to the sample. In order to avoid optical and mechanical disturbances by larger blood components (e.g. erythrocytes) when measuring in whole blood, it is advantageous to cover the end of the light conductor with a thin protein-permeable membrane. Such a membrane permits the passage of proteins while preventing the influence of erythrocytes. Cellulose membranes can be regarded as an ideal material for this purpose.

Of course, for measurements in-vivo by way of optical fibers only those methods are appropriate, for which no harmful additives like acids and fluorescence quencher, etc., have to be added.

It is appropriate to fill the sample cell with water for the following reasons: Firstly, the invading serum is diluted thereby, so that inner filter effects disappear which occur with undiluted sera. Concentration gradients, which may occur, are negligible because of the short measuring time (about 2 sec). Secondly, the danger of introducing air bubbles into the material to be investigated is reduced.

DESCRIPTION OF THE DRAWINGS

The following is a more detailed description of the invention, in which.

DETAILED DESCRIPTION OF THE PREFERRED EMBODIMENTS

Figure 1:
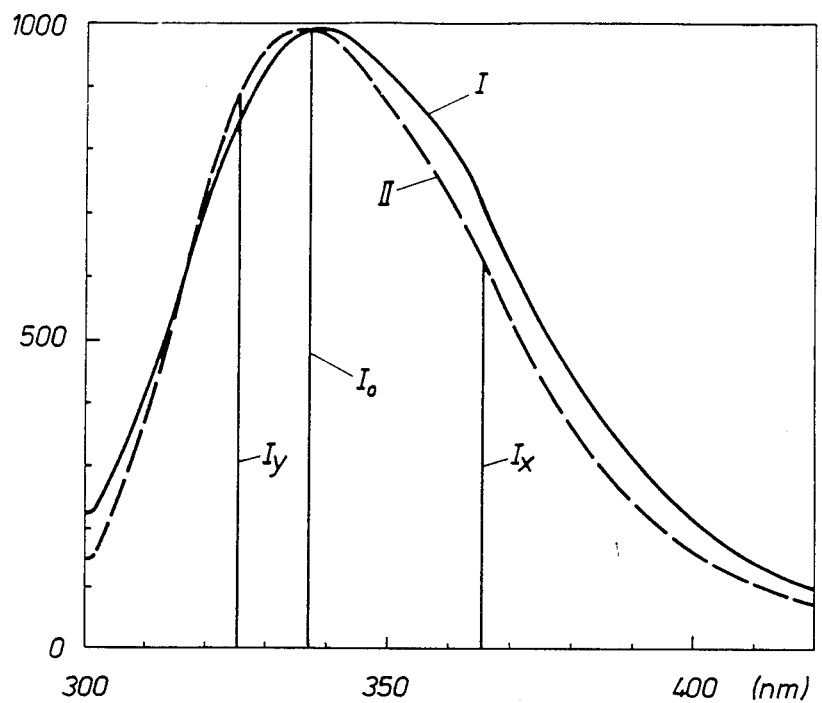
FIGS. 1 to 3 show diagrams of fluorescence spectra.
Figure 2:
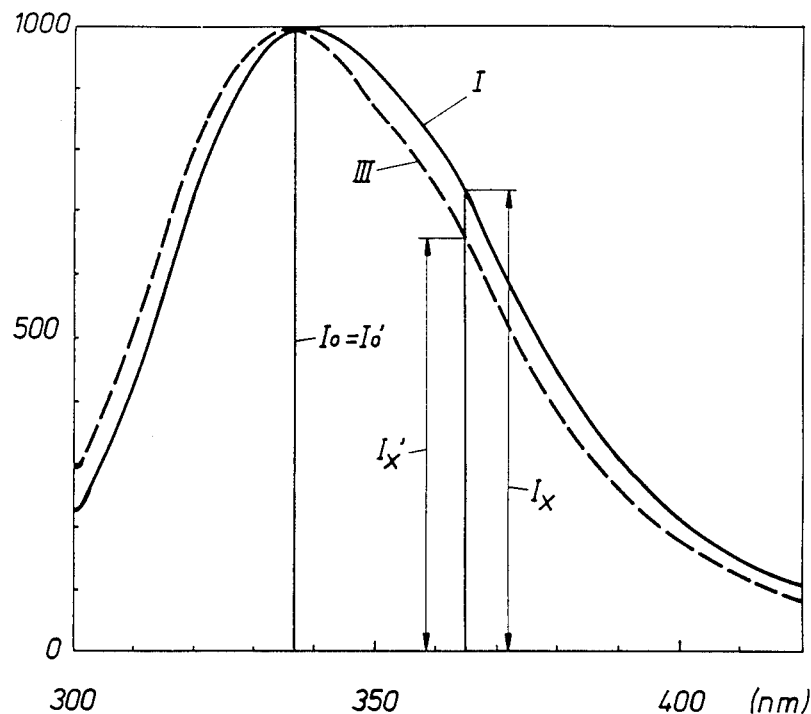
Figure 3:
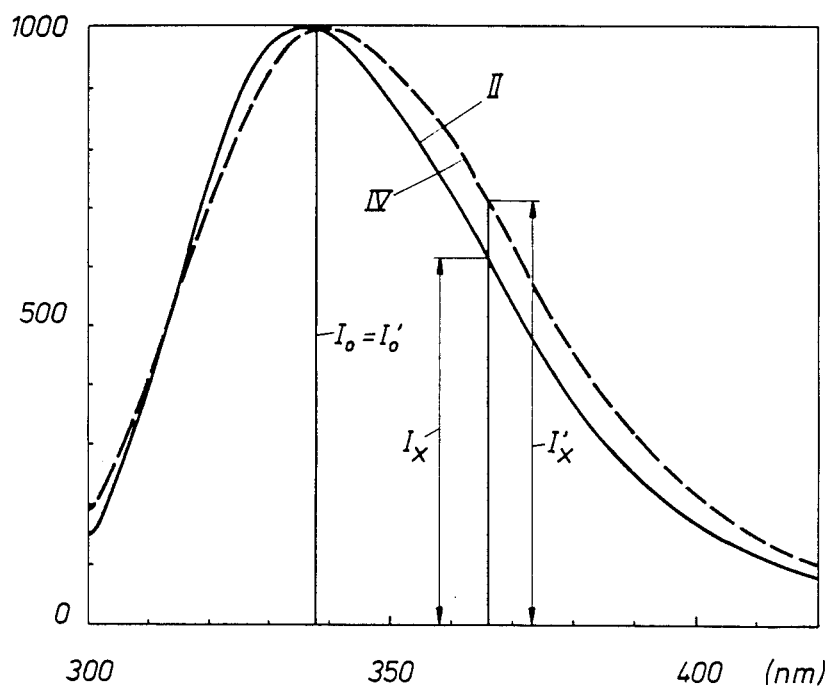

Within the diagrams of FIGS. 1 through 3 the abscissa represents the wavelength in nm and the ordinate represents the fluorescence intensity.

In FIG. 1, a normalized fluorescence spectrum I of human serum is depicted (solid line). It was obtained using an excitation wavelength of 287 nm and shows an emission maximum at 337 nm, which arises predominantly from protein-bound Trp. The band extends over the whole UV-region and partly into the visible region. This is one of the reasons for the bluish-green native fluorescence of serum.

Moreover, it is found that a spectral shift occurs in a fluorescence spectrum II of tumor serum. This can be seen from the broken curve in FIG. 1 which shows, again in normalized form, the emission spectrum of serum from a patient with a gynecological tumor. The intensity of the emission maximum is marked with $I_o$; $I_x$ and $I_y$ are the intensities in the long wavelength (365 nm) and short wavelength (325 nm) region, respectively, of the fluorescence spectrum II of a tumor serum. A falling below and a surpassing, respectively, of the (intensity) values in relation to the fluorescence spectrum I of a normal serum are clearly visible.

FIG. 2 shows typical normalized fluorescence spectra of a normal serum, both at physiological pH-value (7.4) (marked with I) and in 0.1 molar hydrochloric acid (marked with III). It is obvious that a significant blue shift occurs with normal sera when measuring in a highly acidic pH-range.

In contrast to this, normalized fluorescence spectra of a tumor serum are shown in FIG. 3. Spectrum II was measured at 7.4 and spectrum IV in 0.1 molar hydrochloric acid. The Trp emission maximum in acidic solution of sera from patients with malignant tumors is red shifted when compared with those of healthy persons. The intensities are measured both at the emission maximum ($I_o$ and $I_o'$), respectively, and in the long-wavelength range at 365 nm ($I_x$ and $I_x'$), respectively. The symbol (') refers to intensity values measured at acidic pH-value.

Figure 4:
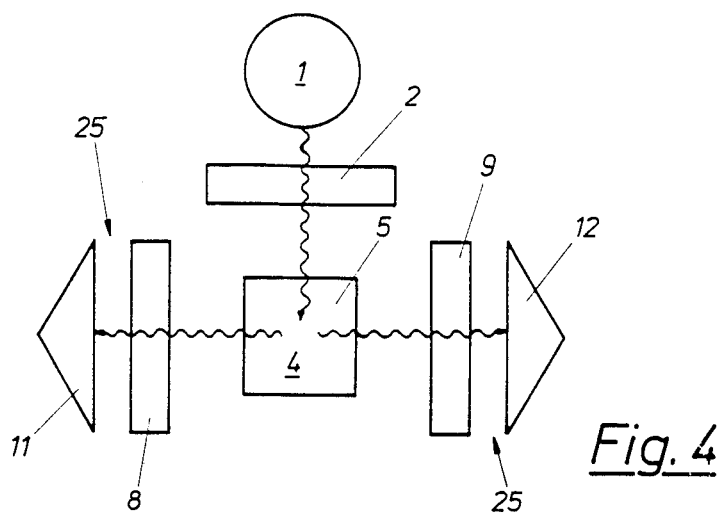
FIGS. 4 to 8 show various arrangements for implementing the method in schematic representation.

The simultaneous determination of the fluorescence intensity at two different wavelengths can be accomplished with an arrangement as outlined in FIG. 4. In this arrangement, light from a light source 1 passes through an excitation filter 2 and reaches a sample 4 (e.g., a serum or a serum protein fraction in a high dilution) in a sample cell 5 which transmits both excitation and emission light. Assuming a sample volume of 2 ml for one measurement, it can be calculated that 2 to 10 ul serum (or 0.2–0.6 mg of its albumin or globulin fraction) are required. From sample cell 5 fluorescence is emitted in all directions. Its intensity is determined at two wavelengths simultaneously with the aid of two measuring devices 25 consisting of optical emission filters 8,9 and two light detectors 11,12.

One optical filter 8 is transmissive to light of wavelength 337 nm and is preferably an interference filter. The other emission filter 9 can be an interference filter or a cut-off filter, which transmits light preferably of a wavelength above 340 nm.

The light intensity is measured with the aid of photodetectors 11 and 12, which can be a photomultiplier tube, a photodiode or a phototransistor. The resultant electric signals are transmitted to a calculator (not shown) and ratioed there.

The ratio of the two light intensities is instrument-dependent and is influenced, inter alia, by the spectral properties of filters 8, 9 as well as by the spectral sensitivity of the amplifiers. At the AMINCO SPF 500 instrument the ratio of intensities at 365 nm and 337 nm is 0.714 +/−0.008 for normal serum (mean of 20 samples).

Figure 5:
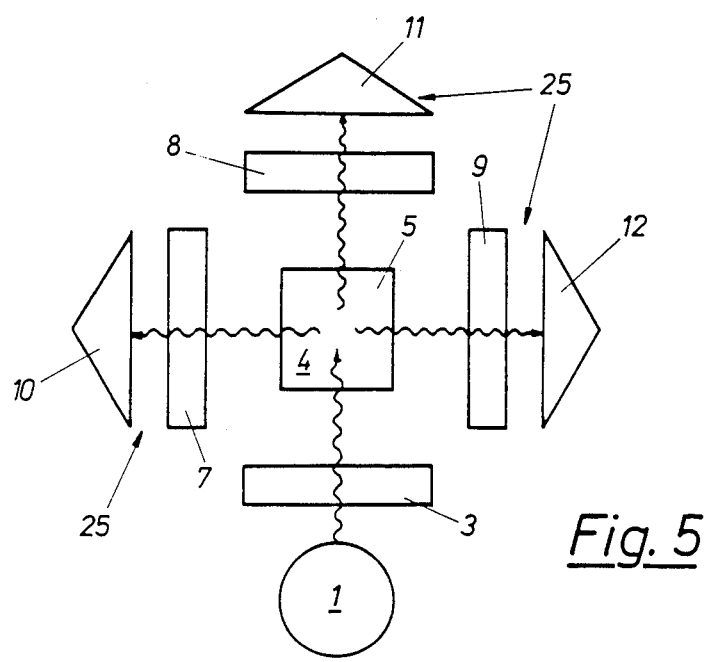

The simultaneous determination of the fluorescence intensities at three different wavelengths can be accomplished with an arrangement as outlined in FIG. 5. In this arrangement, light from a source 1 passes filter 3 which transmits light of a wavelength of typically 295 nm only, and reaches sample 4. The intensity of the emission is now measured at three different wavelengths: At 365 nm an intensity $I_x$ (light filter 9 and detector 12), at 337 nm an intensity $I_o$ (light filter 8 and detector 11) and at 325 nm an intensity $I_y$ (light filter 7 and detector 10).

Figure 6:
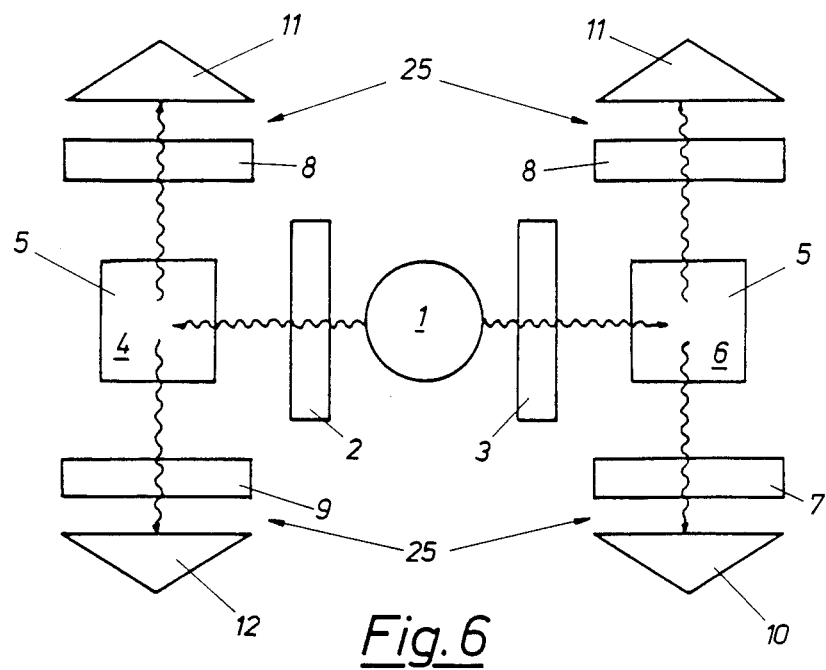

With the aid of the arrangement shown in FIG. 6 it is possible to measure at two excitation wavelengths using two sample cells 5. For that purpose, samples 4 and 6 are filled into the sample cells 5. From light source 1 the excitation light passes first excitation filter 2, which is transmissive for light of wavelength 287 nm, and reaches sample 4. Excitation light of wavelength 295 nm passes a second excitation filter 3 and reaches sample 6. The intensity of the emission is now measured at three different emission wavelengths, namely, at each of the samples 4 and 6 at 337 nm with a light filter 8 and a detector 11 the fluorescence intensities $I_o$ and $I_o'$, respectively. The light filters 9 and 7 transmit light of wavelengths 365 and 325, respectively, and fluorescence intensities $I_x$ and $I_y$ are measured at the detectors 12 and 10, respectively.

It has to be mentioned that the analytical wavelengths given above are instrument-specific and are influenced by the spectral properties of light source and photoamplifier. When using other optical components than those of the instrument mentioned above (e.g., when a deuterium lamp serves as a light source and another photomultiplier tube as detector), slight deviations are to be expected at the wavelengths at which maximum changes occur when compared with normal sera.

With the aid of the arrangement shown in FIG. 6 it is also possible to measure at neutral and acidic pH values simultaneously. For this purpose, however, the excitation filter 3 has to be replaced by a filter 2, as well as emission filter 7 by filter 9 and detector 10 by detector 12. The light from a light source 1 passes light filters 2 and reaches an acidified sample 6 and a neutral sample 4, respectively. Fluorescence, which is emitted from both sample cells into all directions of space, passes optical filters 8 and 9, respectively. The fluorescence intensity is determined simultaneously with the aid of two light detectors each, 11 and 12, respectively, at two different wavelengths. The optical filters 8 again transmit light of wavelength 337 nm and yield fluorescence intensities $I_o$ and $I_o'$; the optical filters 9 transmit light of wavelength 365 nm and yield the fluorescence intensities $I_x$ and $I_x'$.

Figure 7:
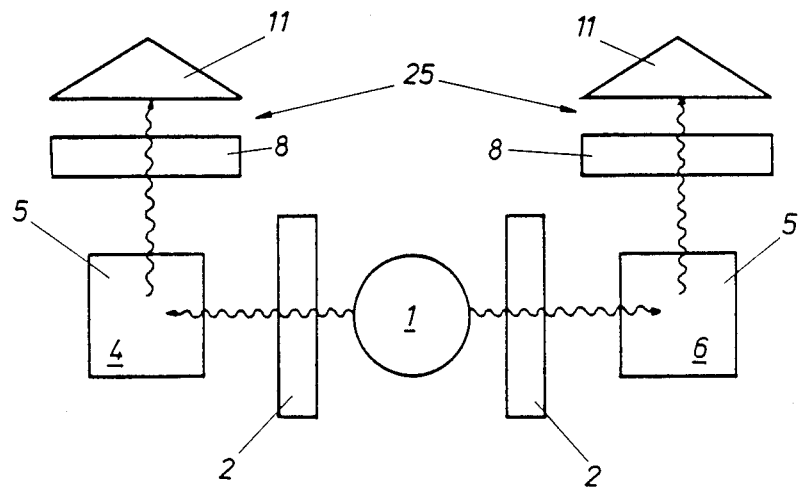

In FIG. 7 an arrangement is depicted which shows the measurement with the aid of the fluorescence quencher method at one analytical wavelength. From the light source 1 the excitation light passes two optical filters 2 to reach samples 4, 6 within the sample cells 5. Sample 4 contains diluted serum, sample 6 contains serum equally diluted and the quencher additive. From both of the samples 4, 6 the fluorescence radiation is emitted into all directions of space. The fluorescence intensities of both samples are determined at the emission wavelength 337 nm (or at a longer wavelength) with the aid of appropriate optical filters and are set into relation in a division unit. The ratio $I/I_o$ will be higher in case of a serum from a tumor-bearing person compared with the corresponding ratio determined with a standard.

An arrangement according to FIG. 6 serves for the measurement at two analytical wavelengths. Light from source 1 reaches the two samples 4, 6 and their respective fluorescence is determined at the analytical wavelengths with the aid of two optical filters each and two photodetectors.

Figure 8:
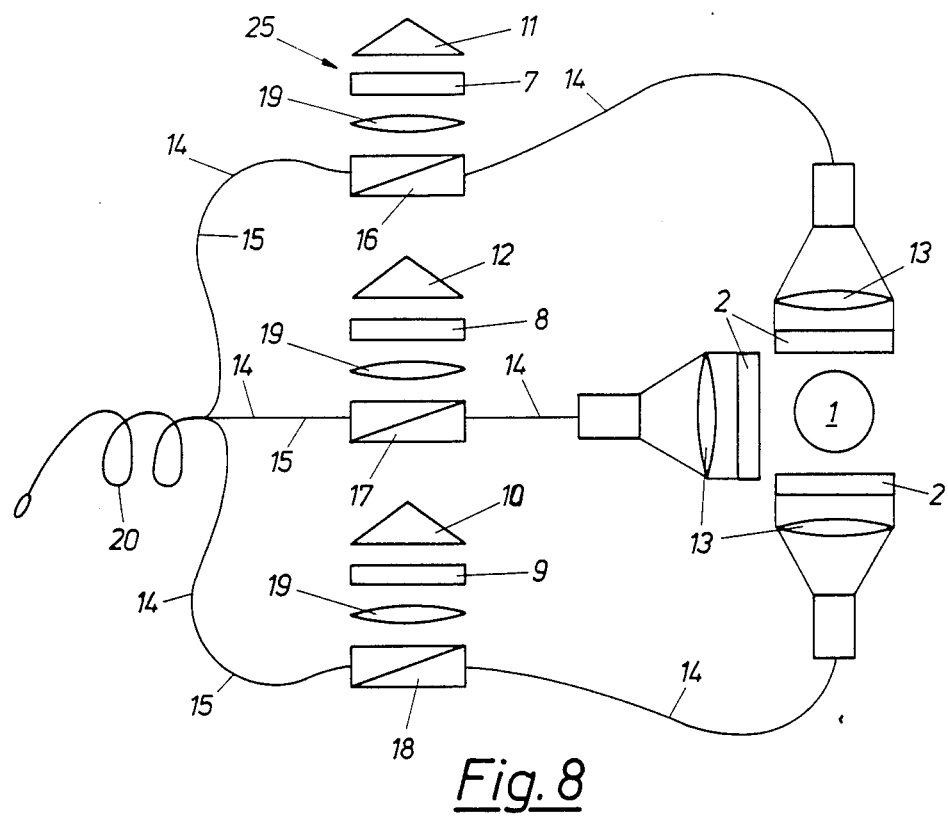

FIG. 8 shows an arrangement similar to FIG. 5, but making possible an in-vivo measurement. After passing optical filters 2, light from a source 1 giving excitation wavelengths of 290 to 295 nm is coupled into light guides 14 with the aid of lenses 13. The light guides 14 transmit the excitation light to the site of measurement. The induced fluorescence light reaches the light detection devices by way back through light guide 15. It is also possible, as depicted in FIG. 8, to guide the excitation and fluorescence light for each emission wavelength to be measured in one light guide and to direct the fluorescence light with the aid of a dichroic mirror or deflecting mirrors 16, 17, 18 onto one of the lenses 19. After passage through filters 7, 8 and 9, adjusted to 325, 337 and 365 nm, respectively, in the individual measuring devices 25, the respective intensity I is determined and evaluated, as described earlier. The end pieces of the light conductors 15 are preferably combined to a catheter-type bundle 20. For compensation of intensity variations a reference photodetector can be coupled to light source 1.

Figure 9:
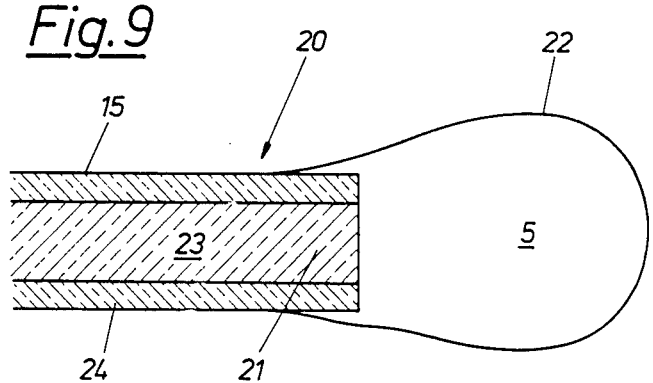
FIG. 9 shows a detail from FIG. 8 in enlarged scale.

FIG. 9 shows the end piece 21 of a light guide 15 consisting of a catheter-type bundle 20 with a balloon-like cellulose membrane 22, which prevents the access of cellular components into sample cell 5, whereas blood serum can diffuse into it. The light guide 15 includes a core 23 and a cladding 24 light guide 15, respectively.

We claim:

1. A method for tumor diagnosis which comprises the steps of (a) exciting a serum to be investigated with excitation radiation with at least one excitation wavelength between 250 and 300 nm, (b) measuring a first fluorescence intensity value of said serum at an emission wavelength of above 340 nm, (c) normalizing said first fluorescence intensity value with respect to fluorescence intensity at fluorescence maximum between 335 and 340 nm to provide a first normalized fluorescence intensity value, (d) comparing said first normalized fluorescence intensity value with a normalized fluorescence intensity value of a standard or standard serum, and (e) concluding from step (d) whether or not the presence of neoplastic diseases is indicated.

2. A method according to claim 1, including the steps of (b') measuring a second fluorescence intensity value of said serum at an emission wavelength between 320 and 330 nm, (c') normalizing said second fluorescence intensity value to provide a second normalized fluorescence intensity value, (d') comparing said second normalized fluorescence intensity value with the normalized fluorecence intensity of a standard serum, and (e')

concluding from step (d') whether or not the presence of neoplastic diseases is indicated.

3. A method for tumor diagnosis which comprises the steps of (a) exciting a serum to be investigated with excitation radiation using at least one excitation wavelength between 250 and 300 nm, (b) measuring fluorescence intensity values of said serum both in physiological and in acidic solution at pH-value below 4, (c) normalizing said fluorescence intensity values with respect to fluorescence intensity at fluorescence maximum between 335 and 340, and (d) concluding from the difference or the ratio of said normalized fluorescence intensity value on the presence of neoplastic diseases.

4. A method for tumor diagnosis which comprises the steps of (a) exciting a serum to be investigated with excitation radiation with at least one excitation wavelength between 250 and 300 nm, (b) measuring fluorescence intensity values of said serum at at least one emission wavelength both in presence and in absence of a dynamic fluorescence quencher, and (c) concluding from the difference or the ratio of said fluorescence intensity values on the presence of neoplastic diseases.

5. A method according to claim 4, wherein iodide ions are used as dynamic fluorescence quenchers in step (b).

6. A method according to claims 1, 2, 3, 4 or 5, wherein in step (a) an albumin subfraction of said serum is excited by excitation radiation.

7. A method according to claims 1, 2, 3, 4 or 5, wherein in step (a) said serum is diluted before measurement.

8. A method according to claims 1, 2, 3, 4 or 5, wherein in step (a) said serum is excited with excitation radiation of two different excitation wavelengths, preferably at 287 and 295 nm, and wherein in steps (b) and (b') fluorescence intensity values are measured at three different emission wavelengths, preferably at 325, 337 and 365 nm.

9. A tumor diagnosis apparatus wherein a serum to be investigated is exposed to excitation radiation, comprising a light source; at least one sample cell containing samples of said serum to be investigated, each said sample cell being located so as to be exposed to said excitation radiation emitted from said light source; at least one excitation filter situated between said light source and each of said sample cells for transmitting at least one excitation wavelenghth between 250 and 300 nm; at least one measuring device comprising an emission filter and a light detector for measuring a first fluorescence intensity value of the serum in said sample cell(s) at an emission wavelength of above 340 nm; and an evaluation unit to which each of said light detectors is connected for normalizing said first fluorescence intensity values with respect to the fluorescence intensity at fluorescence maximum between 335 and 340 nm, for comparing said normalized value with the normalized fluorescence intensity value of a standard or standard serum, and for concluding from a decrease of said first normalized fluorescence intensity value on the presence of neoplastic diseases.

10. A tumor diagnosis apparatus wherein a serum to be investigated is exposed to excitation radiation, comprising a light source; a first and second sample cell containing samples of said serum to be investigated, the serum sample in said first sample cell being a solution having a physiological pH and the serum sample in said second sample cell being in an acidic solution at a pH below 4; a first and a second excitation filter for exciting the samples in said first and second sample cell to at least one excitation wavelength between 250 and 300 nm; at least one measuring device comprising an emission filter and a light detector for measuring fluorescence intensity values of the serum samples in each of said first and second sample cells; and an evaluation unit to which each of said light detectors is connected for normalizing said fluorescence intensity at fluorescence maximum between 335 and 340 nm and for concluding from the difference or the ratio of said normalized fluorescence intensity values on the presence of neoplastic diseases.

11. A tumor diagnosis apparatus wherein a serum to be investigated is exposed to excitation radiation, comprising a light source; a first and second sample cell containing samples of said serum to be investigated, the serum sample in said second sample cell being mixed with a dynamic fluorescence quencher; a first and a second excitation filter for exciting the samples [in said first and second sample cells] in said first and second sample cells to at least one excitation wavelength between 250 and 300 nm; at least one measuring device comprising an emission filter and a light detector for measuring fluorescence intensity values of the samples in each of said first and second sample cells at at least one emission wavelength; and an evaluation unit to which each of said light detectors is connected for concluding from the difference or the ratio of said fluorescence intensity values on the presence of neoplastic diseases.

12. A tumor diagnosis apparatus according to claims 9, 10 or 11, including light guides for said excitation radiation located between each of said sample cells and said light source, and further light guides conducting said emission radiation emitted by said sample to each of said measuring devices.

13. A tumor diagnosis apparatus according to claims 12, wherein each of said sample cells comprises a protein-permeable membrane attached to an end of the associated light guide which is in contact with said sample.

14. A tumor diagnosis apparatus according to claim 9, 10 or 11, including one light guide for each of said measuring devices for conducting both said excitation and said emission radiation, and a dichroic mirror or a ray separator coupling said emission radiation from reflected or scattered excitation light and deflecting said emission readiation to said measuring device.

* * * * *